US008623298B2

(12) United States Patent  (10) Patent No.: US 8,623,298 B2
Leckebusch  (45) Date of Patent: Jan. 7, 2014

(54) SYRINGE WITH EXCHANGEABLE NEEDLE

(75) Inventor: Klaus Leckebusch, Masein (CH)

(73) Assignee: Hamilton Bonaduz AG, Bonaduz (CH)

( * ) Notice: Subject to any disclaimer, the term of this patent is extended or adjusted under 35 U.S.C. 154(b) by 762 days.

(21) Appl. No.: 12/679,056

(22) PCT Filed: Sep. 19, 2008

(86) PCT No.: PCT/EP2008/007911
§ 371 (c)(1),
(2), (4) Date: Jun. 25, 2010

(87) PCT Pub. No.: WO2009/036994
PCT Pub. Date: Mar. 26, 2009

(65) Prior Publication Data
US 2010/0312194 A1 Dec. 9, 2010

(30) Foreign Application Priority Data
Sep. 19, 2007 (DE) ............... 20 2007 013 096 U

(51) Int. Cl.
B01L 3/02 (2006.01)
G01N 1/22 (2006.01)
G01N 1/00 (2006.01)
G01N 35/00 (2006.01)

(52) U.S. Cl.
USPC .......... 422/524; 422/512; 73/863.32; 73/864; 73/864.87

(58) Field of Classification Search
USPC .................................. 422/512, 524
See application file for complete search history.

(56) References Cited

U.S. PATENT DOCUMENTS

| 4,490,142 | A | * | 12/1984 | Silvern | 604/241 |
| 4,740,205 | A | * | 4/1988 | Seltzer et al. | 604/192 |
| 5,195,985 | A | * | 3/1993 | Hall | 604/195 |
| 2007/0027232 | A1 | * | 2/2007 | Walsh et al. | 523/218 |

FOREIGN PATENT DOCUMENTS

WO  2004047895 A  6/2004
WO  2006096901 A  9/2006

* cited by examiner

Primary Examiner — Jill Warden
Assistant Examiner — Brittany Fisher
(74) Attorney, Agent, or Firm — Rothwell, Figg, Ernst & Manbeck, P.C.

(57) ABSTRACT

A syringe comprises a syringe body (12) having an axial inner recess (14) extending in the direction of a longitudinal axis of the syringe body (L), a piston (16) being guided in an axially moveable manner in said inner recess and contributing to the delimitation of a fluid-receiving volume together with a section of a wall (14a) radially delimiting the inner recess (14), and having a needle (24) that can be or is connected to a longitudinal end (12a) of the syringe body (12), wherein the needle (24) has a coupling geometry (28) at the longitudinal end (24a) thereof that is closer to the syringe body, wherein the needle (24) can be connected by said coupling geometry to a counter coupling geometry (30) of the syringe body (12), wherein the geometry composed of the coupling geometry (28) and counter coupling geometry (30) comprises an insertion section (32), which in the assembled state of the syringe (10) is received in a coupling recess (34) of the respectively other geometry, and wherein furthermore safety means (46) are provided, preventing a retraction movement of the insertion section (32) from the coupling recess (34) in the assembled state of the syringe (10).

29 Claims, 2 Drawing Sheets

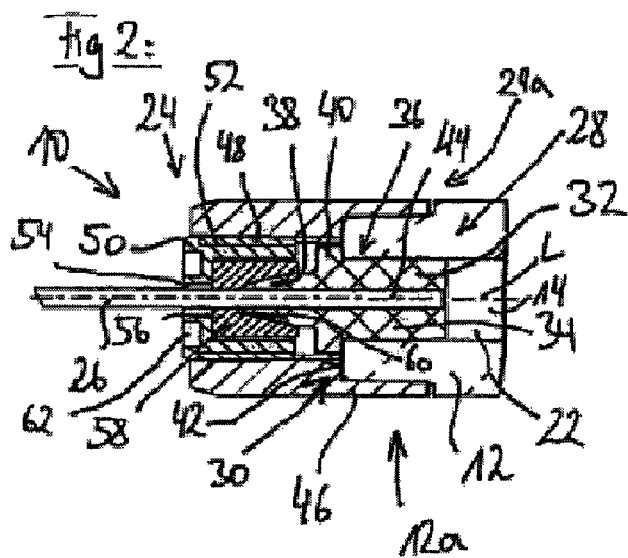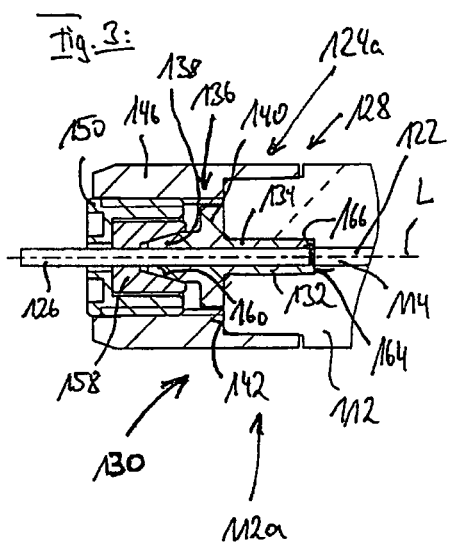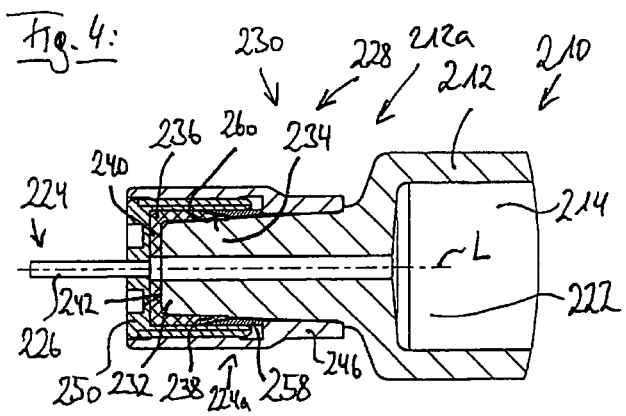

SYRINGE WITH EXCHANGEABLE NEEDLE

CROSS REFERENCE TO RELATED APPLICATION

Figure 1:
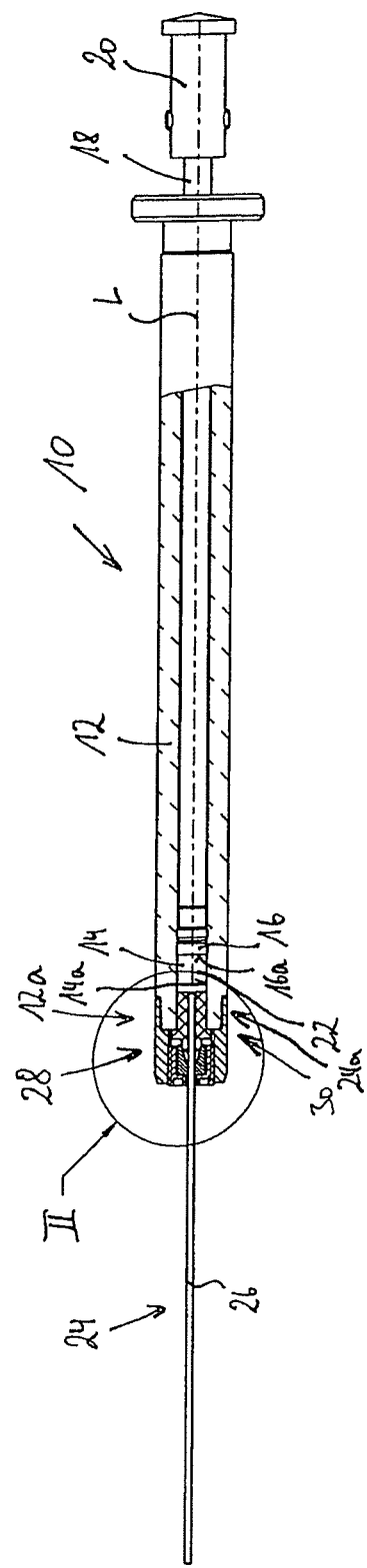

This application is a 35 U.S.C. 371 National Phase Entry Application from PCT/EP2008/07911, filed Sep. 19, 2008, which claims the benefit of German Patent Application No. 20 2007 013 096.1 filed on Sep. 19, 2007, the disclosures of which are incorporated herein in their entirety by reference.

The present invention relates to a syringe, as is used for instance for sample processing in chromatography and the like. Such a syringe comprises a syringe body, which comprises an axial internal recess extending in the direction of a longitudinal axis of the syringe body, in which recess a piston is guided in an axially mobile manner. Together with a portion of a wall radially defining the internal recess, this piston contributes to the delimitation of a fluid receiving volume. The longitudinal axis of the syringe body here basically defines the axial direction. A direction orthogonal thereto is a radial direction for the purposes of the present invention.

Furthermore, such a syringe comprises a needle, which may be or is connected to a longitudinal end of the syringe body.

Syringes are known in principle from the field of medicine in which a needle comprises a coupling geometry at its longitudinal end adjacent the syringe body, by which the needle may be connected to a mating coupling geometry of the syringe body. In the case of the medical syringes known from the prior art the mating coupling geometry comprises an insertion portion, which is accommodated in a coupling recess of the coupling geometry when the syringe is in the assembled state.

The needle/syringe body couplings known from medicine are not sufficient for laboratory applications. They do not fulfil the necessary requirements for strength and above all tightness, such that the purity of a fluid to be received and discharged by the syringe is not satisfactorily ensured.

It is therefore the object of the present invention further to develop syringes known from the prior art in such a way that the above-stated disadvantages are overcome.

According to the present invention this object is achieved by a syringe of the above-mentioned type, for which securing means are provided which prevent a withdrawal movement of the insertion portion out of the coupling recess when the syringe is in the assembled state.

As a result of the securing means provided, the needle can no longer be removed from the syringe body, such that the needle is reliably coupled together with the syringe body.

Securing of the needle to and detachment thereof from the syringe body and a particularly preferred sealing of the needle/syringe body coupling may be achieved in that the securing means comprise an axial adjustment component, which may be displaced by actuation in the axial direction, such that the axial adjustment component may exert axial pressure on the insertion portion introduced into the coupling recess.

The advantageous sealing of the needle/syringe body coupling may be increased still further in that the securing means comprise a clamping geometry which, when the syringe is in the assembled state, is in engagement with a mating clamping geometry associated with the needle.

The clamping geometry and the mating clamping geometry may be brought particularly simply and reliably into sealing engagement with one another when a geometry consisting of clamping geometry and mating clamping geometry comprises a first tapered portion, which tapers towards the free longitudinal end of the geometry bearing it and which, when the syringe is in the assembled state, is introduced at least in portions into a receiving recess of the in each case other geometry, and the receiving recess comprises a first widened portion, which widens towards the free longitudinal end of the geometry bearing it, the taper profile of the first tapered portion in the axial direction and the widening profile of the first widened portion in the axial direction preferably corresponding substantially in such a way that, when the syringe is in the assembled state, the tapered portion rests in linear manner at least along a circumferential line around the syringe body longitudinal axis, particularly preferably rests extensively against the widened portion along a circumferential contact surface.

Constructionally, provision may here be made for the first tapered portion to comprise a cone portion and for the receiving recess preferably to comprise a conical recess. Particularly preferably, the cone portion and the conical recess have the same cone opening angle.

To reduce the number of components required for producing the syringe, provision may be made for the clamping geometry to be formed integrally on the axial adjustment component.

On the other hand, assembly of the syringe components with one another may be effected particularly gently with regard to said components if the clamping geometry is formed on a clamping component provided separately from the axial adjustment component, which clamping component may be displaced axially by the axial adjustment component. In this case relative motion may be brought about purposefully at non-critical points and be reduced between syringe components at critical points, so reducing the risk of damage to components.

Particularly good sealing of the needle relative to the syringe body and the surrounding environment, with simultaneous correct positioning of the needle relative to the syringe body, may be ensured according to a first further development of the present invention in that a component displaying the clamping geometry is configured for joint movement with the needle. According to an alternative second further development of the present invention, at least correct positioning of the needle relative to the syringe body may also be ensured in that the axial adjustment component is configured for joint movement with the needle.

Configuration of a component "for joint movement" with the needle may be achieved either by one-piece construction of the component with the needle or by rigid connection of the component with the needle.

For advantageous, maximally exact positioning of the axial adjustment component, provision may be made for the latter to be guided for axial movement on a guide component.

From a structural standpoint, the guide component may comprise a sleeve, which is provided on the syringe body, in particular at the longitudinal end thereof nearer the needle.

For particularly secure connection of the guide component to the syringe body, it is conceivable for the guide component, in particular the sleeve, to be connected to the syringe body by pressing and/or adhesive bonding.

Particularly simple, secure and at the same time precise positioning of the axial adjustment component relative to the guide component may be achieved in that the guide component, in particular the sleeve, comprises a thread, preferably an internal thread, and in that the axial adjustment component comprises a screw, which comprises a mating thread, preferably an external thread, in or capable of being brought into engagement with said thread. Positioning accuracy here depends on the selected pitch of the thread and mating thread.

Preferably, the thread of the guide component is an internal thread, such that the axial adjustment component may be screwed thereinto. This avoids the syringe being excessively large radially.

To achieve a modular syringe construction, which is advantageous because it can be adapted in each case to the respective instance of use, the coupling geometry may be provided on a separate coupling component.

For defined positioning of the coupling component in the axial direction and thus to ensure a coupling and sealing action as good as possible, it is feasible for the coupling component to comprise a projection, preferably a radial projection, for resting on a mating contact face of the syringe body.

The sealing action which may be achieved with the coupling component may be further increased in that said component is made from a resilient material. In this case the insertion portion, if provided on the coupling component, may comprise a cylindrical portion, for simplifying insertion into the coupling recess, optionally with an insertion bevel, the cylindrical portion of the insertion portion then being inserted into the coupling recess and coming to lie sealingly against an associated wall of the coupling recess by clamping by means of the above-stated clamping geometry.

It is likewise feasible to configure the insertion portion with a bulging external shape, such that radial pretensioning may be achieved purely on the basis of resilient material deformation on insertion of the insertion portion into the coupling recess. However, gaps at the point at which the coupling component is coupled to the syringe body should be avoided, since materials may accumulate here which may contaminate the fluid accommodated in the fluid receiving volume therein in the case of a plurality of successive filling operations.

It is likewise feasible to make the coupling component from a rigid material and to bring the rigid coupling component to rest sealingly against a likewise rigid mating coupling geometry on the syringe body.

Both in the case of the insertion portion and the coupling recess being made from rigid materials and in the case of at least one of the constructions being made from a resilient material, such as for instance polytetrafluoroethylene, a good sealing action of the coupling point between coupling geometry and mating coupling geometry may be achieved in that the insertion portion comprises a second tapered portion, which tapers towards the free longitudinal end of the geometry bearing it and which is inserted at least in portions into the coupling recess of the in each case other geometry when the syringe is in the assembled state, and in that the coupling recess comprises a second widened portion, which widens towards the free longitudinal end of the geometry bearing it, the taper profile of the second tapered portion in the axial direction and the widening profile of the second widened portion in the axial direction preferably corresponding substantially in such a way that, when the syringe is in the assembled state, the second tapered portion rests in linear manner at least along a circumferential line around the syringe body longitudinal axis, particularly preferably rests extensively against the second widened portion along a circumferential contact surface. In this case even small taper or widening angles may lead to the desired coupling and sealing results.

From a manufacturing standpoint, the insertion portion particularly simply and therefore preferably comprises a cone portion and the coupling recess preferably comprises a conical recess.

The sealing action of the coupling point may be still further increased in that the insertion portion comprises an end face with radial extension component, which rests sealingly against a mating face of the syringe body when the syringe is in the assembled state. However, it is also recommendable, to avoid undesirable double fits, for at least one of the geometries participating in coupling to be made from a resilient material.

Particularly when the syringe described here is used in a laboratory, in particular in chromatography, it is very important to avoid contamination of the fluid drawn up in the syringe. To this end provision may be made for at least some of the surfaces, preferably all the surfaces of the syringe, which during use thereof come into contact with a fluid to be received and/or discharged by the syringe, to be provided with a coating. This coating may be a quartz or glass coating, these providing a particularly smooth surface which is inert relative to a large number of fluids and at the same time transparent. The coating may be applied by "nano technology" on the inside and/or outside of the needle. The coating may be applied in a manner known per se by a sol-gel process to the walls or wall portions in question of the syringe.

The present invention is described in greater detail below with reference to the attached drawings, in which:

FIG. 1 shows a partially sectional view of a first embodiment of a syringe according to the invention, FIG. 2 shows a longitudinally sectional detail view of the needle/syringe body coupling of the first embodiment of FIG. 1, FIG. 3 shows a second embodiment of a needle/syringe body coupling and FIG. 4 shows a third embodiment of a needle/syringe body coupling.

FIG. 1 shows a first embodiment of a syringe according to the invention, designated overall as 10. The syringe 10 comprises a syringe body 12 with an internal recess 14 extending in the direction of the longitudinal axis L of a syringe body, in which recess a piston 16 is accommodated so as to be movable in the direction of the longitudinal axis L of the syringe body, i.e. in an axial direction.

The piston 16 is movable by a piston rod 18 connected rigidly to the piston 16, which piston rod 18 may be pull- and push-actuated by means of an actuating end member 20.

A piston face 16a directed towards the longitudinal end 12a of the syringe body 12 nearer to the needle contributes, together with a portion 14a of a circumferential wall defining the internal recess 14 in the radial direction, to delimitation of a fluid receiving volume 22.

The syringe 10 shown in FIG. 1 further comprises a needle 24, with a needle cannula 26. In the assembled state, the needle 24 comprises a coupling geometry 28 at its longitudinal end 24a nearer to the syringe body which is in engagement with a mating coupling geometry 30 at the longitudinal end 12a of the syringe body 12 nearer to the needle to couple the needle 24 to the syringe body 12.

The detailed configuration of the coupling of the needle 24 to the syringe body 12 is shown in FIG. 2. FIG. 2 shows the detail encircled in FIG. 1 and labelled "II".

In the first exemplary embodiment shown in FIG. 2 the coupling geometry 28 comprises a substantially cylindrical insertion portion 32, which has been introduced into a coupling recess 34 in the mating coupling geometry 30. To simplify insertion of the insertion portion 32 into the coupling recess 34, the insertion portion 32 is provided at its longitudinal end introduced into the coupling recess 34 with an insertion bevel or a circumferential insertion chamfer.

The insertion portion 32 is an integral part of a coupling component 36 made from resilient plastics, in the present example polytetrafluoroethylene.

This component 36 comprises a mating clamping geometry 38 in the form of a clamping cone at its opposite longitudinal end from the insertion portion 32.

A radial projection 40 is formed axially on the coupling component 36, encircling the latter in the circumferential direction, between the mating clamping geometry 38 and the insertion portion 32, said radial projection resting against a mating contact face 42 of the syringe body 12 when the syringe 10 is in the assembled state. If the radial projection 40 comes to rest against the mating contact face 42, correct seating of the coupling component 36 is ensured.

The needle cannula 26 is inserted into a central through-recess 44 of the coupling component 36.

In principle, the needle cannula 26 may be connected to the coupling component 36 by adhesive bonding or the like. Preferably, to prevent undesired contamination of a fluid accommodated in the fluid receiving chamber 22 with constituents of the adhesive, the needle cannula 26 is retained merely by non-positive or frictional engagement in the coupling component 36.

A sleeve-type guide component 46 is connected to the syringe body 12 by being pressed and adhesively bonded onto a radial shoulder at the longitudinal end 12a of the syringe body 12.

The guide component 46 comprises an internal thread 48, into which an axial adjustment component in the form of a clamping screw 50 with an external thread 52 is screwed in axially movable manner along the longitudinal axis L of the syringe body.

The needle cannula 26 is fed through a central recess 54, the diameter of the central recess 54 being greater than the external diameter of the needle cannula 26.

In a cup-shaped recess 56 in the clamping screw 50 there is accommodated a clamping component 58, which is adhesively bonded, welded or otherwise connected to the needle cannula 26 for joint movement.

The clamping component 58 comprises a clamping geometry in the form of a conical receiving recess 60, into which the conical mating clamping geometry 38 of the coupling component 36 protrudes in the axial direction.

By turning the clamping screw 50 by means of a into the tool engagement recesses 62 at the end face of the clamping screw 50 remote from the syringe body towards the syringe body 12, the resilient coupling component 36 may be purposefully resiliently deformed, such that it rests sealingly without a gap against the coupling component 12.

In the first exemplary embodiment shown in FIG. 2 the coupling recess 34 develops continuously into the internal recess 14.

FIG. 3 shows an alternative second exemplary embodiment. Components which are the same as in FIG. 2 are provided with the same reference numerals but increased by the number 100.

The embodiment of FIG. 3 is described hereinafter only to the extent that it differs from the embodiment of FIGS. 1 and 2, to the description of which express reference is made.

The second embodiment, which is illustrated in FIG. 3, is suitable for syringes with an extremely small syringe volume, i.e. with an internal recess 114 with a very small diameter.

It is apparent that the coupling recess 134 has a larger diameter than the internal recess 114 in the syringe body 112.

The coupling recess 134 therefore develops into the internal recess 114, forming a radial step. An end face 164 of the insertion portion 132 may thus come to rest sealingly against a mating face 166 of the syringe body 112, if sufficient deformation pressure is exerted on the coupling component 136 by means of the clamping screw 150 and the clamping component 158.

FIG. 4 shows a third embodiment of a syringe according to the invention with a needle/syringe body coupling.

Components which are the same as in the embodiments of FIGS. 1 to 3 are provided in the third embodiment according to FIG. 4 with the same reference numerals, but increased by the number 200 or 100 respectively. The third embodiment is only described insofar as it differs from the first two embodiments, to the description of which express reference is otherwise made.

In the embodiment shown in FIG. 4 the insertion portion 232 is provided on the mating coupling geometry 230 of the syringe body 212, while the coupling recess 234 is formed in the coupling geometry 228 of the needle 224.

Unlike in the previous embodiments, the radial projection 240 of the coupling component 236 extends radially inwards at the longitudinal end of the coupling component 236 remote from the syringe body.

Also in contrast to the preceding embodiments, the clamping component 258 is supported axially against the sleeve-type guide component 264.

The clamping screw 250 is connected for joint rotation with the needle cannula 226.

The mating clamping geometry 238 of the coupling component 236 surrounds the insertion portion 234 of the syringe body 212 radially on the outside in the circumferential direction and rests against the conical receiving recess 260 of the clamping component 258.

The invention claimed is:

1. A syringe comprising:
a syringe body having a longitudinal axis, wherein the syringe body comprises
an axial internal recess extending in the direction of the longitudinal axis of the syringe body, and
a piston, positioned in the axial internal recess, which is guided in an axially mobile manner, wherein the piston, together with a portion of a wall radially defining the axial internal recess, contributes to the delimitation of a fluid receiving volume,
a syringe body mating coupling geometry located at a longitudinal end of the syringe body,
a needle having a longitudinal end,
a needle coupling geometry, located at the longitudinal end of the needle towards the syringe body, which mates the needle to the syringe body mating coupling geometry, and wherein the needle coupling geometry comprises
an insertion portion, wherein, when the syringe is in an assembled state, the insertion portion is accommodated in a coupling recess, and
a securing means which prevents a withdrawal movement of the insertion portion out of the coupling recess when the syringe is in the assembled state, wherein the securing means prevents removal of the needle from the syringe body when the syringe is in the assembled state, and wherein the securing means comprises a clamping geometry such that when the syringe is in the assembled state, the clamping geometry is in engagement with a mating clamping geometry which is configured to contact the needle.

2. A syringe according to claim 1, wherein the securing means comprises an axial adjustment component, which is displaced by actuation in the axial direction.

3. A syringe according to claim 1, wherein the mating clamping geometry comprises a first tapered portion, which tapers away from the syringe body and which, when the syringe is in the assembled state, is introduced, at least in portions, into a receiving recess of the clamping geometry, wherein the receiving recess comprises a first widened portion, which widens towards the syringe body, and wherein the taper profile of the first tapered portion in the axial direction and the widening profile of the first widened portion of the receiving recess in the axial direction substantially correspond such that, when the syringe is in the assembled state, the first tapered portion rests in a linear manner at least along a circumferential line around the syringe body longitudinal axis against the first widened portion of the receiving recess along a circumferential contact surface.

4. A syringe according to claim 3, wherein the first tapered portion comprises a cone portion and the receiving recess comprises a conical recess.

5. A syringe according to claim 3, wherein the clamping geometry is formed integrally on the axial adjustment component.

6. A syringe according to claim 3, wherein the clamping geometry is formed on a clamping component provided separately from the axial adjustment component, wherein the clamping component is displaceable axially by the axial adjustment component.

7. A syringe according to claim 5, wherein a clamping component comprising the clamping geometry is configured for joint movement with the needle.

8. A syringe according to claim 2, wherein the axial adjustment component is configured for joint movement with the needle.

9. A syringe according to claim 2, wherein the axial adjustment component is configured to be guided on a guide component for axial movement.

10. A syringe according to claim 9, wherein the guide component comprises a sleeve, which is provided on the longitudinal end of the syringe body towards the needle.

11. A syringe according to claim 9, wherein the guide component is connected to the syringe body by pressing and/or adhesive bonding.

12. A syringe according to claim 9, wherein the guide component comprises a thread, and wherein the axial adjustment component comprises a screw, and wherein the screw comprises a mating thread, capable of being brought into engagement with the thread of the guide component.

13. A syringe according to claim 1, wherein the needle coupling geometry is a separate coupling component.

14. A syringe according to claim 13, wherein the coupling component comprises a projection, for resting against a mating contact face of the syringe body.

15. A syringe according to claim 13, wherein the coupling component is made from a resilient material.

16. A syringe according to claim 1, wherein the insertion portion comprises a tapered portion, which tapers towards the syringe body and which is inserted, at least in portions, into the coupling recess when the syringe is in the assembled state, and wherein the coupling recess comprises a widened portion, which widens away from the syringe body, and wherein the taper profile of the tapered portion in the axial direction and the widening profile of the widened portion of the coupling recess in the axial direction substantially correspond such that, when the syringe is in the assembled state, the tapered portion rests in a linear manner at least along a circumferential line around the syringe body longitudinal axis against the widened portion of the coupling recess along a circumferential contact surface.

17. A syringe according to claim 16, wherein the insertion portion comprises a cone portion and the coupling recess comprises a conical recess.

18. A syringe according to claim 1, wherein the insertion portion comprises an end face with a radial extension component, which rests sealingly against a mating face of the syringe body when the syringe is in the assembled state.

19. A syringe according to claim 1, wherein at least one of the surfaces of the syringe, which during use thereof come into contact with a fluid to be received and/or discharged by the syringe, are provided with a coating.

20. A syringe according to claim 19, wherein the coating is a quartz or glass coating.

21. A syringe according to claim 19, wherein a surface of the needle, is provided with a coating applied by a nano technology process.

22. A syringe according to claim 12, wherein the guide component comprises an internal thread.

23. A syringe according to claim 12, wherein the screw comprises an external mating thread.

24. A syringe according to claim 13, wherein the coupling component comprises a radial projection, for resting against a mating contact face of the syringe body.

25. A syringe comprising:
a syringe body having a longitudinal axis, wherein the syringe body comprises
an axial internal recess extending in the direction of the longitudinal axis of the syringe body, and
a piston, positioned in the axial internal recess, which is guided in an axially mobile manner, wherein the piston, together with a portion of a wall radially defining the axial internal recess, contributes to the delimitation of a fluid receiving volume,
a syringe body mating coupling geometry located at a longitudinal end of the syringe body,
a needle having a longitudinal end,
a needle coupling geometry, located at the longitudinal end of the needle towards the syringe body, which mates the needle to the syringe body mating coupling geometry, and wherein the needle coupling geometry comprises
an insertion portion, wherein, when the syringe is in an assembled state, the insertion portion is accommodated in a coupling recess, and
a securing means which prevents a withdrawal movement of the insertion portion out of the coupling recess when the syringe is in the assembled state, wherein the securing means prevents removal of the needle from the syringe body when the syringe is in the assembled state, and wherein the securing means comprises an axial adjustment component, which is displaced by actuation in the axial direction,
wherein the axial adjustment component is configured to be guided on a guide component for axial movement, and
wherein the guide component comprises a sleeve, which is provided on the longitudinal end of the syringe body towards the needle.

26. A syringe comprising:
a syringe body having a longitudinal axis, wherein the syringe body comprises
an axial internal recess extending in the direction of the longitudinal axis of the syringe body, and
a piston, positioned in the axial internal recess, which is guided in an axially mobile manner, wherein the piston, together with a portion of a wall radially defining the axial internal recess, contributes to the delimitation of a fluid receiving volume,
a syringe body mating coupling geometry located at a longitudinal end of the syringe body,
a needle having a longitudinal end, a needle coupling geometry, located at the longitudinal end of the needle towards the syringe body, which mates the needle to the syringe body mating coupling geometry, and wherein the needle coupling geometry comprises
an insertion portion, wherein, when the syringe is in an assembled state, the insertion portion is accommodated in a coupling recess, and
a securing means which prevents a withdrawal movement of the insertion portion out of the coupling recess when the syringe is in the assembled state, wherein the securing means prevents removal of the needle from the syringe body when the syringe is in the assembled state, and wherein the securing means comprises an axial adjustment component, which is displaced by actuation in the axial direction,
wherein the axial adjustment component is configured to be guided on a guide component for axial movement, and
wherein the guide component is connected to the syringe body by pressing and/or adhesive bonding.

27. A syringe comprising:
a syringe body having a longitudinal axis, wherein the syringe body comprises
an axial internal recess extending in the direction of the longitudinal axis of the syringe body, and
a piston, positioned in the axial internal recess, which is guided in an axially mobile manner, wherein the piston, together with a portion of a wall radially defining the axial internal recess, contributes to the delimitation of a fluid receiving volume,
a syringe body mating coupling geometry located at a longitudinal end of the syringe body,
a needle having a longitudinal end,
a needle coupling geometry, located at the longitudinal end of the needle towards the syringe body, which mates the needle to the syringe body mating coupling geometry, and wherein the needle coupling geometry comprises
an insertion portion, wherein, when the syringe is in an assembled state, the insertion portion is accommodated in a coupling recess, and
a securing means which prevents a withdrawal movement of the insertion portion out of the coupling recess when the syringe is in the assembled state, wherein the securing means prevents removal of the needle from the syringe body when the syringe is in the assembled state, and wherein the securing means comprises an axial adjustment component, which is displaced by actuation in the axial direction,
wherein the axial adjustment component is configured to be guided on a guide component for axial movement, and
wherein the guide component comprises a thread, and wherein the axial adjustment component comprises a screw, and wherein the screw comprises a mating thread, capable of being brought into engagement with the thread of the guide component.

28. A syringe comprising:
a syringe body having a longitudinal axis, wherein the syringe body comprises
an axial internal recess extending in the direction of the longitudinal axis of the syringe body, and
a piston, positioned in the axial internal recess, which is guided in an axially mobile manner, wherein the piston, together with a portion of a wall radially defining the axial internal recess, contributes to the delimitation of a fluid receiving volume,
a syringe body mating coupling geometry located at a longitudinal end of the syringe body,
a needle having a longitudinal end,
a needle coupling geometry, located at the longitudinal end of the needle towards the syringe body, which mates the needle to the syringe body mating coupling geometry, and wherein the needle coupling geometry comprises
an insertion portion, wherein, when the syringe is in an assembled state, the insertion portion is accommodated in a coupling recess, and
a securing means which prevents a withdrawal movement of the insertion portion out of the coupling recess when the syringe is in the assembled state, wherein the securing means prevents removal of the needle from the syringe body when the syringe is in the assembled state,
wherein the insertion portion comprises a tapered portion, which tapers towards the syringe body and which is inserted, at least in portions, into the coupling recess when the syringe is in the assembled state, and wherein the coupling recess comprises a widened portion, which widens away from the syringe body, and wherein the taper profile of the tapered portion in the axial direction and the widening profile of the widened portion of the coupling recess in the axial direction substantially correspond such that, when the syringe is in the assembled state, the tapered portion rests in a linear manner at least along a circumferential line around the syringe body longitudinal axis against the widened portion of the coupling recess along a circumferential contact surface.

29. A syringe according to claim 28, wherein the insertion portion comprises a cone portion and the coupling recess comprises a conical recess.

* * * * *

UNITED STATES PATENT AND TRADEMARK OFFICE
CERTIFICATE OF CORRECTION

PATENT NO. : 8,623,298 B2  Page 1 of 1
APPLICATION NO. : 12/679056
DATED : January 7, 2014
INVENTOR(S) : Klaus Leckebusch It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 860 days.

Signed and Sealed this
Twenty-second Day of September, 2015

Michelle K. Lee
*Director of the United States Patent and Trademark Office*